United States Patent [19]

Klein et al.

[11] Patent Number: 4,888,446

[45] Date of Patent: Dec. 19, 1989

[54] PREPARATION OF POLYOXYALKYLENE GLYCOL AMINES

[75] Inventors: Howard P. Klein; Michael Cuscurida, both of Austin, Tex.

[73] Assignee: Texaco Chemical Co., White Plains, N.Y.

[21] Appl. No.: 179,827

[22] Filed: Apr. 11, 1988

[51] Int. Cl.$^4$ .......................................... C07C 85/06
[52] U.S. Cl. .................................. 564/478; 564/474; 564/475; 564/477; 568/902; 568/903
[58] Field of Search ............... 564/474, 475, 477, 478

[56] References Cited

U.S. PATENT DOCUMENTS

| | | | |
|---|---|---|---|
| 3,110,732 | 11/1963 | Speranzo et al. | 260/584 |
| 3,231,619 | 1/1966 | Speraenza | 260/584 |
| 3,317,609 | 5/1967 | Lesesne | 260/584 |
| 3,335,186 | 8/1967 | Speranza | 260/584 |
| 3,382,284 | 5/1968 | Schulze | 260/613 |
| 3,393,243 | 7/1968 | Cuscurida | 260/615 |
| 3,535,307 | 10/1970 | Moss et al. | 260/209 |
| 3,654,370 | 4/1972 | Yeakey | 260/584 B |
| 3,954,873 | 5/1976 | Gipson | 260/584 |
| 4,111,924 | 9/1978 | Fujimo et al. | 260/112.5 R |
| 4,150,243 | 4/1979 | Brück et al. | 568/805 |
| 4,166,172 | 8/1979 | Klein | 536/4 |
| 4,228,310 | 10/1980 | Speranza et al. | 568/620 |
| 4,228,311 | 10/1980 | Dodd | 568/751 |
| 4,487,853 | 12/1984 | Reichel et al. | 521/172 |
| 4,612,335 | 9/1986 | Cuscurida et al. | 564/477 |
| 4,665,236 | 5/1987 | Edwards | 564/475 |

OTHER PUBLICATIONS

"Protective Groups in Organic Synthesis," John Wiley and Sons, 1981, pp. 81-82.
"Nafion-H" Catalyzed Di-t-butylation of Aromatic Compounds, J. Org. Chem. 52, 1881-4, 1987.

Primary Examiner—Glennon H. Hollrah
Assistant Examiner—Ba K. Trinh
Attorney, Agent, or Firm—Jack H. Park; Kenneth R. Priem

[57] ABSTRACT

The invention concerns a method for the preparation of polyoxyalkylene compounds wherein each compound has one primary amine group and one primary hydroxyl group. The method comprises alkoxylating a t-butyl ethylene, propylene or butylene glycol then aminating the product. Finally the t-butyl group is cleaved by an acid. The compounds of the method of this invention are useful in urethane/urea plastics including foams, elastomers and coatings.

6 Claims, No Drawings

PREPARATION OF POLYOXYALKYLENE GLYCOL AMINES

RELATED APPLICATION

This application is related to application Ser. No. 07/179,826 and application Ser. No. 7/179,828 filed of even date.

FIELD OF THE INVENTION

The invention relates to methods for preparing amino alcohol.

BACKGROUND OF THE INVENTION

Amino alcohols are desirable and well known types of compounds, U.S. Pat. No. 3,231,619 describes a method for manufacturing amino alcohols as does U.S. Pat. No. 4,612,335.

It would be desirable to provide a facile method for manufacturing amino alchols which contain a primary amine group and a primary hydroxyl group on each molecule.

SUMMARY OF THE INVENTION

A method of preparing polyoxyalkylene compounds of about 200 to 400 molecular weight which have a primary amine group and a primary hydroxyl group said compounds having the structure:

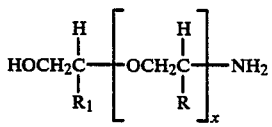

where
x=0–50
R=H, CH$_3$, C$_2$H$_5$
comprising reacting a compound of the formula

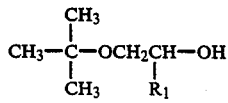

where R$_1$ is H, —CH$_3$ or —CH$_2$CH$_3$ with ethylene oxide, propylene oxide and/or 1,2-butylene oxide or mixtures thereof, aminating the product of said reaction and then cleaving the t-butyl group of the aminated compound with an acidic reagent.

DESCRIPTION OF THE PREFERRED EMBODIMENTS

The method of our invention is the manufacture of a polyoxyalkylene polymer in the range of about 200 to 4000 molecular weight which have in each molecule a primary amine group at one end and a primary hydroxyl group at the other. This can be accomplished by the use of three known reactions by careful selection of starting materials and reactants. The reaction scheme is shown below:

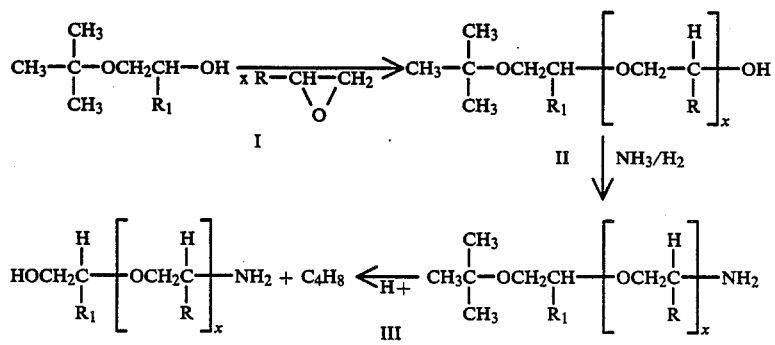

R=H, CH$_3$, C$_2$H$_5$
R$_1$=H, CH$_3$, C$_2$H$_5$
x=0–50

In reaction I the alkoxylation of a blocked ethylene, propylene or butylene glycol is shown. In order to obtain the primary hydroxyl group on the final amino alcohol the tertiary butyl (t-butyl) ether is preferred. The epoxide may be ethylene oxide, propylene oxide or butylene oxide. Alkoxylation reactions are known in the art and are catalyzed by potassium or sodium hydroxides, for example, U.S. Pat. No. 3,535,307 describes typical alkoxylation techniques useful in this invention and is incorporated by reference. Other known methods for alkoxylation are acceptable for this invention. The degree of alkoxylation will determine the molecular weight of the product. The type of epoxide used will also help determine the solubility characteristics of the final material. It is known, for example, that ethylene oxide adducts are usually more water soluble than propylene oxide adducts and butylene oxide adducts. The desirable molecular weight will be determined by the amount of epoxide added in order to serve the purpose of the end user. Thus, those skilled in the art will be able to adjust both the water solubility and the molecular weight of the material in reaction I.

Reaction II is the amination of the alkoxylated material from the reaction I. This amination of polyoxyalkylene alcohols is described for example in U.S. Pat. No. 3,654,370. This patent is incorporated by reference.

The aminated alcohol, which is the result of reaction II, is then reacted with a strong acid such as hydrochloric acid. Enough acid is necessary to neutralize the amine and enough excess to provide the acid conditions necessary for cleavage on the t-butyl group. Those skilled in the art will be able to determine the proper conditions for cleavage to take place. Conditions may range from about room temperature to about 150° C. and pressure low enough to allow the cleaved isobutylene to escape the reacting mixture. For example, atmospheric is acceptable but any pressure which achieves the results described is acceptable. As a result the tertiary butyl end part of the molecule is cleaved and replaced by a primary hydroxyl group. Thus, the result of this reaction scheme is the manufacture of a variable molecular weight polyoxyalkylene amino alcohol which contains a primary hydroxyl group at one end and a primary amine group at the other end. The acidic groups useful in the cleavage reaction III were found to be materials such as hydrochloric acid or hydrobromic acid. It was found that other materials such as sulfuric acid, Amberlyst ®15 (acidic ion exchange resin), Zeolite ®ZM-8 (sodium aluminum phosphate), and salts of a polyether amine and Amberlyst ®15 did not work as well.

Examples follow which show the method of the invention.

EXAMPLE 1

This example will illustrate the preparation of a 550 molecular weight propylene oxide adduct of propylene glycol t-butyl ether (Arcosolv PTB, ARCO Chemical Co.)

Six pounds propylene glycol t-butyl ether were charged into a ten-gallon kettle. The reactor was then purged with prepurified nitrogen. The reactor was then heated to 75° C. and 45.4 g flaked potassium hydroxide was added to the kettle and stirred until it was solubilized. At this point the water content of the charge was 0.295%. It was then nitrogen stripped to a water content of 0.1% or less. Propylene oxide (21.3 lb) was then reacted at 105°–115° C. at 50 psig. Approximately four hours was required for addition of the propylene oxide. The reaction mixture was then digested two hours to an equilibrium pressure. The alkaline product was then neutralized at 95° C. by stirring two hours with 270 g Magnesol 30/40 which was added as an aqueous slurry. The neutralized product was then stabilized with 6.2 g di-t-butyl-p-cresol, vacuum and nitrogen stripped and filtered. The finished product had the following properties:

| Properties | |
|---|---|
| Acid no., mg KOH/g | 0.003 |
| Hydroxyl no., mg KOH/g | 102 |
| Water, wt. % | 0.002 |
| pH in 10:6 isopropanol/water | 8.1 |
| Color, Pt—Co | 25 |
| Sodium, ppm | 0.5 |
| Potassium, ppm | 0.3 |
| Viscosity, °F., cs | |
| 77 | 47.6 |
| 100 | 27.1 |

EXAMPLE 2

This example will demonstrate the reductive amination of the 550 molecular weight propylene oxide adduct of propylene glycol t-butyl ether prepared in Example 1.

Into a 1250 ml tubular reactor filled with a nickel oxide-copper oxide-chromium oxide catalyst were fed the polyether (0.8 lb/hr), ammonia (1.20 lb/hr), and hydrogen (48 l/hr). The reactor was kept at 190° C. and the pressure was 2000 psig. The crude reactor effluent was then stripped at 70° C. and 3.5 mm Hg for 30 minutes. The resultant product had the following properties:

| Properties | |
|---|---|
| Total amine, meq/g | 1.75 |
| Primary amine, meq/g | 1.75 |
| Total acetylatables, meq/g | 1.74 |

EXAMPLE 3

Into a 500 ml three-necked flask equipped with a stirrer, thermometer, water condenser and nitrogen source were charged 200 g of the aminated polyether of Example 2 and 93.6 g of 15% aqueous hydrochloric acid. The reaction temperature immediately rose to 58° C. at which point heat was applied and the reaction mixture heated at 92°–100° C. for 3.75 hrs. The product was then neutralized with 144 g of 15% aqueous potassium hydroxide. The neutralized product was then vacuum stripped to a minimum pressure at 112° C. for one hour and filtered with the aid of Hyflo Supercel. The filtered product was a dark yellow liquid which had the following properties:

| Total amine, meq/g | 2.0 |
|---|---|
| Total acetylatables, meq/g | 3.3 |

The carbon 13 nmr spectra of the product was consistent with the following structure:

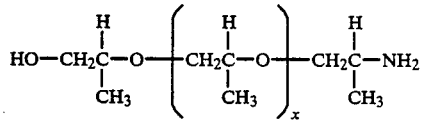

$x = \sim 8$

EXAMPLE 4

Using the procedure outlined in Example 1, a polyether alcohol was made using the following reaction sequence:

Propylene glycol t-butyl ether + 8 moles EO + 10 moles PO.

The product had the following properties:

| Acid no., mg KOH/g | 0.001 |
|---|---|
| Hydroxyl no., mg KOH/g | 65 |
| Water, wt % | 0.13 |
| pH in 10:6 isopropanol-water | 7.9 |
| Color, Pt—Co | 50 |
| Sodium, ppm | 0.5 |
| Potassium, ppm | 1.2 |
| Viscosity, °F., cc | |
| 77 | 108 |
| 100 | 61.3 |

EXAMPLE 5

The polyether alcohol of Example 4 was reductively aminated over the nickel-copper-chromium catalyst described in Example 2 at 210° C., 2000 psig, and a liquid space velocity of 0.75 g/cc-cat/hr. Ammonia was 60% of the liquid feed so the polyol space velocity was 0.30 g/cc-cat/hr. Properties of the aminated polyether were as follows:

| Properties | |
|---|---|
| Total acetylatables, meq/g | 1.14 |
| Total amine, meq/g | 1.09 |
| Primary amine, meq/g | 1.09 |
| Color, Pt—Co | 20 |

EXAMPLE 6

This example will demonstrate the cleavage of the polyetheramine of Example 5 to form the corresponding amino alcohol. It will further show that the reaction can be monitored (disappearance of t-butyl group) using $^{13}C$ NMR.

Into a two-liter four-necked flask equipped with a stirrer, thermometer, water condenser, and nitrogen source were charged 500 g of the polyetheramine and 139.5 g 15% aqueous hydrochloric acid. The reaction mixture was then heated over a 40-minute period to 105° C. and held at 104°–107° C. over a three-hour period. Vigorous evolution of isobutylene occurred at 100°–105° C. An additional 6.6 g 15% hydrochloric acid was added to the reaction mixture which was heated an additional hour at 105° C. Samples were withdrawn at one-hour intervals for $^{13}C$ NMR analysis. At the end of the reaction, the product was neutralized by stirring with 75 g 45% aqueous potassium hydroxide and 34 g Magnesol 30/40. The neutralized product was then vacuum stripped to 125° C. and 5 mm Hg and filtered with the aid of Hyflo Supercel filter aid. The finished product was a light yellow viscous liquid with the following properties:

| Total acetylatables, meq/g | 2.25 |
|---|---|
| Total amine, meq/g | 1.14 |
| Water, wt % | 0.033 |

The $^{13}C$ NMR spectra of the product was consistent with the following structure:

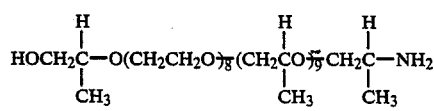

The extent of cleavage, as monitored by $^{13}C$ NMR, was as follows:

| Time, hr | t-Butyl cleavage, % |
|---|---|
| 0 | 0 |
| 1 | 59 |
| 2 | 61 |
| 3 | 72 |
| 4 | 98 |

EXAMPLE 7

This example will demonstrate a scale-up preparation of an amino alcohol by removal of the t-butyl group from the polyether amine of Example 5.

5.2 lb of the polyetheramine were charged into a three-gallon kettle which was then purged with prepurified nitrogen. Fifteen percent aqueous hydrochloric acid (689.3 g) was then added to the polyether amine and the mixture heated to 105°–110° C. for six hours. The kettle was vented to the flare during that period as isobutylene was liberated during the reaction. An additional 31.3 g of the 15% hydrochloric acid was then added to the kettle and the mixture heated an additional two hours at 105°–110° C. The reaction mixture was then neutralized with 369.9 g 45% aqueous potassium hydroxide and stirred an additional two hours with 166.4 g Magnesol ®30/40 which was added as an aqueous slurry. The product was then vacuum stripped to a minimum pressure, nitrogen stripped and filtered with the aid of a filter acid. The finished product was a dark yellow viscous liquid which had the following properties:

| Total amine, meq/g | 1.102 |
|---|---|
| Total acetylatables, meq/g | 2.232 |
| Water, wt % | 0.18 |
| pH in 10:6 isopropanol-water | 11.5 |
| Sodium, ppm | 5.8 |
| Potassium, ppm | 19 |
| Viscosity, °F., cs | |
| 77 | 139 |
| 100 | 72.6 |

The NMR spectra of the product indicated that 95% of the t-butyl group had been removed.

I claim:

1. A method for preparing polyoxyalkylene compounds of about 200 to 4000 molecular weight which have a primary amine group and a primary hydroxyl group said compounds having the structure:

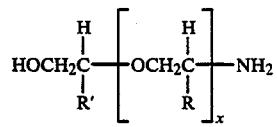

where
R' is H, —CH$_3$, C$_2$H$_5$ and
x is 0–50
comprising reacting a compound of the formula

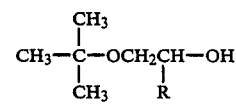

where R is H, —CH$_3$ or —CH$_2$CH$_3$ with ethylene oxide, propylene oxide or 1,2-butylene oxide or mixtures thereof, aminating the product of said reaction and then cleaving the t-butyl group of the aminated compound with a halogen acid.

2. A method as in claim 1 where R is H or CH$_3$.
3. A method as in claim 1 where R is CH$_3$.
4. A method as in claim 1 where x is about 8.
5. A method for preparing a compound of the formula

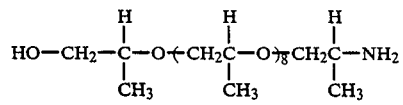

comprising reacting a compound of the formula

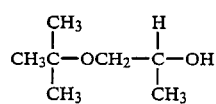

with propylene oxide, aminating the product of the reaction and then cleaving the t-butyl group of the aminated compound with a halogen acid.

6. A method for preparing a compound of the formula

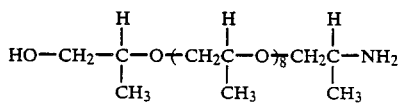

comprising reacting a compound of the formula

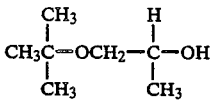

with propylene oxide and ethylene oxide aminating the product of the reaction and then cleaving the t-buty group of the aminated compound with a halogen acid.

* * * * *